United States Patent
Thesman

(12) 
(10) Patent No.: US 10,467,719 B2
(45) Date of Patent: Nov. 5, 2019

(54) METHODS FOR ADMINISTERING PREVENTATIVE HEALTHCARE TO A PATIENT POPULATION

(71) Applicant: Debra Thesman, Marina Del Rey, CA (US)

(72) Inventor: Debra Thesman, Marina Del Rey, CA (US)

(73) Assignee: QUALITY STANDARDS, LLC, Wilmington, DE (US)

( * ) Notice: Subject to any disclaimer, the term of this patent is extended or adjusted under 35 U.S.C. 154(b) by 0 days.

(21) Appl. No.: 16/351,034

(22) Filed: Mar. 12, 2019

(65) Prior Publication Data
US 2019/0213701 A1 Jul. 11, 2019

Related U.S. Application Data

(63) Continuation of application No. 13/715,869, filed on Dec. 14, 2012, now Pat. No. 10,242,416, which is a continuation of application No. 13/712,758, filed on Dec. 12, 2012.

(51) Int. Cl.
*G06Q 50/22* (2018.01)
*G16H 50/30* (2018.01)
*G16H 50/70* (2018.01)

(52) U.S. Cl.
CPC ........... *G06Q 50/22* (2013.01); *G16H 50/30* (2018.01); *G16H 50/70* (2018.01)

(58) Field of Classification Search
CPC ........ G16H 10/60; G16H 40/20; G16H 50/30; G16H 50/70; G16H 50/20; G06Q 50/24; G06Q 10/0635; G06F 19/325; G06F 19/3456
See application file for complete search history.

(56) References Cited

U.S. PATENT DOCUMENTS

| | | |
|---|---|---|
| 5,544,044 A | 8/1996 | Leatherman |
| 5,576,755 A | 11/1996 | Davis et al. |
| 6,009,408 A | 12/1999 | Buchanan |

(Continued)

FOREIGN PATENT DOCUMENTS

CA 2846501 3/2013

OTHER PUBLICATIONS

WayBackMachine, www.coastlineelderly.org, Jun. 18, 2004—Index. htm, Mission.htm, Info.htm, Services.htm, Shine.htm.

(Continued)

*Primary Examiner* — Maroun P Kanaan
(74) *Attorney, Agent, or Firm* — Stetina Brunda Garred & Brucker

(57) ABSTRACT

Methods for administering preventative healthcare measures to a patient population are disclosed. A patient population eligible to receive certain healthcare benefits is defined and thereafter multiple sources of healthcare data are compiled and analyzed to create health profiles for each individual. An objective set of criteria for providing preventative care is provided to eligible members within the patient population and appropriate healthcare is administered to the degree necessary to make sure a sufficient percentage of the population receives adequate healthcare treatment consistent with the recognized, objective healthcare standards. Patients remaining non-compliant are sought for further administration of healthcare until requisite compliance standards are met.

5 Claims, 3 Drawing Sheets

(56) References Cited

U.S. PATENT DOCUMENTS

| | | |
|---|---|---|
| 6,014,629 A | 1/2000 | DeBruin-Ashton |
| 6,067,524 A | 5/2000 | Byerly |
| 6,240,394 B1 | 5/2001 | Uecker |
| 6,263,330 B1 | 7/2001 | Bessett |
| 6,283,761 B1 | 9/2001 | Joao |
| 6,298,348 B1 | 10/2001 | Eldering |
| 6,341,265 B1 | 1/2002 | Provost |
| 6,343,271 B1 | 1/2002 | Peterson et al. |
| D454,139 S | 3/2002 | Feldcamp |
| 6,735,569 B1 | 5/2004 | Wizig |
| 6,802,810 B2 | 10/2004 | Ciarniello et al. |
| 6,820,058 B2 | 11/2004 | Wood et al. |
| 6,824,052 B2 | 11/2004 | Walsh |
| D512,017 S | 11/2005 | Esque |
| 7,016,856 B1 | 4/2006 | Wiggins |
| 7,039,458 B2 | 5/2006 | Ueda et al. |
| 7,153,137 B2 | 12/2006 | Altenhofen et al. |
| 7,251,610 B2 | 7/2007 | Alban et al. |
| 7,275,220 B2 | 9/2007 | Brummel et al. |
| D573,599 S | 7/2008 | Williams |
| 7,401,025 B1 | 7/2008 | Lokitz |
| 7,464,041 B2 | 12/2008 | Merkin |
| 7,483,838 B1 | 1/2009 | Marks |
| 7,490,048 B2 | 2/2009 | Joao |
| D593,114 S | 5/2009 | Vakkalanka |
| 7,533,353 B2 | 5/2009 | Dvorak et al. |
| 7,657,442 B2 | 2/2010 | Merkin |
| 7,698,154 B2 | 4/2010 | Marchosky |
| 7,698,155 B1 | 4/2010 | Prasad et al. |
| 7,702,524 B1 | 4/2010 | Whibbs et al. |
| 7,734,656 B2 | 6/2010 | Bessette et al. |
| 7,742,930 B1 | 6/2010 | Calhoun, Jr. et al. |
| 7,801,744 B2 | 9/2010 | Patterson |
| 7,856,456 B2 | 12/2010 | Bessette |
| 7,881,950 B2 | 2/2011 | Petterson |
| 7,899,689 B1 | 3/2011 | Wizig |
| 7,904,313 B2 | 3/2011 | Knight |
| 7,917,438 B2 | 3/2011 | Kennedy et al. |
| D640,265 S | 6/2011 | Brouwers et al. |
| 7,958,002 B2 | 6/2011 | Bost |
| 7,984,079 B2 | 7/2011 | Bessette |
| D644,649 S | 9/2011 | Fullington et al. |
| 8,050,945 B2 | 11/2011 | Patterson |
| 8,060,376 B2 | 11/2011 | Horner |
| 8,073,714 B1 | 12/2011 | Ball |
| D658,667 S | 5/2012 | Cho |
| D667,837 S | 9/2012 | Magee et al. |
| 8,262,394 B2 | 9/2012 | Walker et al. |
| 8,285,565 B2 | 10/2012 | Kerr et al. |
| 8,289,750 B2 | 10/2012 | Krishnan et al. |
| 8,290,789 B2 | 10/2012 | Wennberg |
| 8,296,333 B2 | 10/2012 | Bessette |
| 8,308,062 B1 | 11/2012 | Walton, III |
| 8,311,855 B2 | 11/2012 | Kerr et al. |
| 8,321,239 B2 | 11/2012 | Hansen et al. |
| 8,326,648 B2 | 12/2012 | Kennedy et al. |
| 8,332,466 B1 | 12/2012 | Cha et al. |
| 8,335,696 B2 | 12/2012 | Brown |
| 8,380,631 B2 | 2/2013 | Dala et al. |
| 8,442,840 B2 | 5/2013 | Menocal et al. |
| 8,452,617 B2 | 5/2013 | Kerr et al. |
| 8,756,588 B2 | 6/2014 | Zheng et al. |
| 8,762,181 B1 | 6/2014 | Ringold |
| D708,626 S | 7/2014 | Klein et al. |
| 8,812,533 B1 | 8/2014 | Liggett et al. |
| 8,819,632 B2 | 8/2014 | Williams et al. |
| D748,129 S | 1/2016 | Steplyk |
| D751,106 S | 3/2016 | Chetan et al. |
| D757,779 S | 5/2016 | Steinfeld et al. |
| D774,058 S | 12/2016 | Dias et al. |
| D774,528 S | 12/2016 | Klein et al. |
| D778,935 S | 2/2017 | Scheepers et al. |
| D781,324 S | 3/2017 | Marohn et al. |
| D818,476 S | 5/2018 | Hawkins et al. |
| D820,288 S | 6/2018 | Howell et al. |
| D828,374 S | 9/2018 | Kolbenheyer |
| 2001/0037214 A1 | 11/2001 | Raskin et al. |
| 2001/0042080 A1 | 11/2001 | Ross |
| 2002/0000247 A1 | 1/2002 | Michelson et al. |
| 2002/0007290 A1 | 1/2002 | Gottlieb |
| 2002/0019754 A1 | 2/2002 | Peterson et al. |
| 2002/0026105 A1 | 2/2002 | Drazen |
| 2002/0035316 A1 | 3/2002 | Drazen |
| 2002/0120471 A1 | 4/2002 | Drazen |
| 2002/0052754 A1 | 5/2002 | Joyce et al. |
| 2002/0062226 A1 | 5/2002 | Ito |
| 2002/0072933 A1 | 6/2002 | Vonk et al. |
| 2002/0073207 A1 | 6/2002 | Widger et al. |
| 2002/0120508 A1 | 8/2002 | Matsumoto et al. |
| 2002/0123906 A1 | 9/2002 | Goetzke et al. |
| 2002/0149616 A1 | 10/2002 | Gross et al. |
| 2002/0188689 A1 | 12/2002 | Michael |
| 2003/0023598 A1 | 1/2003 | Janakiraman et al. |
| 2003/0060688 A1 | 3/2003 | Ciarniello et al. |
| 2003/0074228 A1 | 4/2003 | Walsh |
| 2003/0078811 A1 | 4/2003 | Cole et al. |
| 2003/0078813 A1 | 4/2003 | Haskell et al. |
| 2003/0078911 A1 | 4/2003 | Haskell et al. |
| 2003/0097077 A1 | 5/2003 | Morganroth |
| 2003/0105824 A1 | 6/2003 | Brechner et al. |
| 2003/0167183 A1 | 9/2003 | Kido et al. |
| 2003/0167189 A1 | 9/2003 | Lutgen et al. |
| 2003/0182290 A1 | 9/2003 | Parker |
| 2003/0193448 A1 | 10/2003 | Tsui |
| 2003/0200141 A1 | 10/2003 | Robison |
| 2003/0212579 A1 | 11/2003 | Brown et al. |
| 2004/0006530 A1 | 1/2004 | Allamon et al. |
| 2004/0035434 A1 | 2/2004 | Easter |
| 2004/0039600 A1 | 2/2004 | Kramer et al. |
| 2004/0044546 A1 | 3/2004 | Moore |
| 2004/0093223 A1 | 5/2004 | Inman |
| 2004/0103022 A1 | 5/2004 | Chilcoat, III et al. |
| 2004/0122702 A1 | 6/2004 | Sabol et al. |
| 2004/0186744 A1 | 9/2004 | Lux |
| 2004/0196448 A1 | 10/2004 | Rembe et al. |
| 2004/0210471 A1 | 10/2004 | Luby et al. |
| 2005/0010436 A1 | 1/2005 | Merkin |
| 2005/0010440 A1 | 1/2005 | Merkin |
| 2005/0091077 A1 | 4/2005 | Reynolds |
| 2005/0158767 A1 | 7/2005 | Haskell et al. |
| 2005/0202383 A1 | 9/2005 | Thomas et al. |
| 2006/0004651 A1 | 1/2006 | Corr et al. |
| 2006/0031094 A1 | 2/2006 | Cohen et al. |
| 2006/0078533 A1 | 4/2006 | Omoigui |
| 2006/0080146 A1 | 4/2006 | Cook et al. |
| 2006/0085222 A1 | 4/2006 | Huang et al. |
| 2006/0155586 A1 | 7/2006 | Hirshberg |
| 2006/0172429 A1 | 8/2006 | Nilsson et al. |
| 2006/0235280 A1 | 10/2006 | Vonk et al. |
| 2006/0235984 A1 | 10/2006 | Kraus et al. |
| 2006/0281977 A1 | 12/2006 | Soppet |
| 2007/0122783 A1 | 5/2007 | Habashi |
| 2007/0185732 A1 | 8/2007 | Hicks et al. |
| 2007/0203760 A1 | 8/2007 | Schmidt et al. |
| 2007/0214497 A1 | 9/2007 | Montgomery et al. |
| 2007/0244714 A1 | 10/2007 | McCluskey et al. |
| 2008/0004904 A1 | 1/2008 | Tran |
| 2008/0059224 A1 | 3/2008 | Schechter |
| 2008/0086327 A1 | 4/2008 | Cox et al. |
| 2008/0086337 A1 | 4/2008 | Soon-Shiong |
| 2008/0103369 A1 | 5/2008 | Fabius et al. |
| 2008/0162190 A1 | 7/2008 | Ghouri |
| 2009/0012716 A1 | 1/2009 | Urdea et al. |
| 2009/0024417 A1 | 1/2009 | Marks et al. |
| 2009/0113008 A1 | 4/2009 | Gonzalez et al. |
| 2009/0254375 A1 | 10/2009 | Martinez et al. |
| 2010/0017742 A1 | 1/2010 | Rhodes et al. |
| 2010/0030574 A1 | 2/2010 | Coe et al. |
| 2010/0131298 A1 | 5/2010 | Buttner et al. |
| 2010/0217625 A1 | 8/2010 | Dust et al. |
| 2010/0274589 A1 | 10/2010 | Bauer et al. |
| 2010/0028085 A1 | 11/2010 | Merkin |
| 2010/0280851 A1 | 11/2010 | Merkin |
| 2011/0029321 A1 | 2/2011 | Rourke et al. |

(56) References Cited

U.S. PATENT DOCUMENTS

| | | |
|---|---|---|
| 2011/0118555 A1 | 5/2011 | Dhumne et al. |
| 2011/0145018 A1 | 6/2011 | Fotsch et al. |
| 2011/0153348 A1 | 6/2011 | Kerr et al. |
| 2011/0270632 A1 | 11/2011 | Manning et al. |
| 2012/0041786 A1 | 2/2012 | Yu |
| 2012/0078664 A1 | 3/2012 | Hasan et al. |
| 2012/0109681 A1 | 5/2012 | Chapman et al. |
| 2012/0109686 A1 | 5/2012 | Higbie et al. |
| 2012/0191472 A1 | 7/2012 | Thesman |
| 2012/0191487 A1 | 7/2012 | Merkin |
| 2012/0226507 A1 | 9/2012 | Wendt |
| 2012/0265554 A1 | 10/2012 | Ferguson |
| 2012/0278094 A1 | 11/2012 | Kovacevic et al. |
| 2012/0284044 A1 | 11/2012 | Bregante et al. |
| 2012/0284055 A1 | 11/2012 | Hansan et al. |
| 2012/0284056 A1 | 11/2012 | Hofstetter |
| 2012/0284057 A1 | 11/2012 | Hansan et al. |
| 2012/0290322 A1 | 11/2012 | Bergman et al. |
| 2012/0296665 A1 | 11/2012 | Merkin |
| 2012/0303378 A1 | 11/2012 | Liberman |
| 2012/0303381 A1 | 11/2012 | Bessette |
| 2012/0329015 A1 | 12/2012 | Thesman |
| 2012/0330681 A1 | 12/2012 | Olalekan |
| 2013/0024207 A1 | 1/2013 | Anderson et al. |
| 2013/0030838 A1 | 1/2013 | Myers et al. |
| 2013/0041690 A1 | 2/2013 | Brough |
| 2013/0054264 A1 | 2/2013 | Baronov et al. |
| 2013/0124226 A1 | 5/2013 | Gedala |
| 2014/0058755 A1 | 2/2014 | Macoviak et al. |
| 2014/0164003 A1 | 6/2014 | Thesman |
| 2014/0258032 A1 | 9/2014 | Psota et al. |
| 2015/0227278 A1 | 8/2015 | Bruce et al. |
| 2016/0328577 A1 | 11/2016 | Howley |
| 2017/0289199 A1 | 10/2017 | Barday |

OTHER PUBLICATIONS

Gibson, James L. et al.; Organizations: Behavior Structure Processes; 9th Edition, Times Mirror Higher Education Group; Chapter 7; 1997; pp. 176-191.

Grossman, Claudia, et al.; Chapter 5—Healthcare Data as a Public Good; Privacy and Security Clinical Data as the Basic Staple of Health Learning; Creating and Protecting a Public Good; Workshop Summary; 2010; pp. 171-202; The National Academies Press; Washington, DC.

Nat et al., Marketing Fraud: An Approach To Differentiating Multilevel Marketing From Pyramid Schemes, Spring 2002, Journal of Public Policy and Marketing, vol. 21, p. 139-151.

Taking the Bite Out of Dental Readiness: Assessing Readiness in the National Guard and the Reserves, Col. George J. Hucal, Mar. 7, 2009, Department of Veterans Affairs.

www.wiredseniors.com, www.wiredseniors.com pages (Dec. 29, 2004 archived version)(Year: 2004).

www.wiredseniors.com, www.wiredseniors.com pages (Jan. 29, 2005 archived version)(Year: 2005).

www.wiredseniors.com, www.wiredseniors.com pages (May 9, 2008 archived version)(Year: 2008).

Caricone, Making Worksite Marking Work, May 2005, http://www.roughnotes.com/mmagazine/2005/may05/05p142.htm, pp. 1-3.

"21+ Doctors Note Templates—Free Sample, Example, Format Download!" Mar. 12, 2016, posted at template.net [site visted Nov. 28, 2018] https://web.archive.org/web/20160312125432/https://www.template.net/business/note-template/doctor-note-template.

Kohn, Bernard, "Website Wireframe Examples" Jul. 10, 2012, posted at comentum.com [site visited Nov. 28, 2018] https://web.archive.org/web/20120710234307/https://www.conmentum.com/wireframe-example.html.

Wikipedia, http//en.wikipedia.org/wiki/ICD.

Jepsen, IT in Healthcare: Progress Report, Feb. 2003, IT Pro IEEE Computer Society, pp. 8-14. (Year: 2003).

Ackerman et al., Telemedicine Technology, 2002, Telemedicine Journal and e-Health, vol. 8, No. 1, pp. 71-78 (Year: 2002).

CMS, released Aug. 4, 2011, available online at http://www.calquality.org/storage/documents/resources/2012%20specifications%20for%20medicare%20stars%20measures.pdf.

Quality Performance Measures for ACO
Summary Report
For Measurement Year 2012

| Title: Preventative Health | Eligible Population | Compliant | Not Compliant | Rate | Benchmark |
|---|---|---|---|---|---|
| Influenza Immunization | 4285 | 2203 | 2082 | 51% | 90% |
| Pneumococcal Vaccination | 3794 | 769 | 3025 | 20% | 90% |
| Adult Weight Screening and Follow - Up | 2387 | 17 | 2370 | 1% | 90% |
| Tobacco Use and Cessation (queried tobacco use) | 5475 | 0 | 5475 | 0% | 90% |
| Tobacco Use and Cessation (received cessation) | 5490 | 0 | 5490 | 0% | 90% |
| Depression Screening | 5252 | 0 | 5252 | 0% | 90% |
| Colorectal Cancer Screening | 3584 | 1206 | 2378 | 34% | 90% |
| Mammography Screening | 1224 | 490 | 734 | 40% | 90% |
| BP Measurement | 5683 | 0 | 5683 | 0% | 90% |

FIG. 3

METHODS FOR ADMINISTERING PREVENTATIVE HEALTHCARE TO A PATIENT POPULATION

CROSS-REFERENCE TO RELATED APPLICATIONS

The present application is a continuation of U.S. patent application Ser. No. 13/715,869 filed Dec. 14, 2012, which is a continuation of U.S. patent application Ser. No. 13/712,758 filed Dec. 12, 2012, entitled METHODS FOR ADMINISTERING PREVENTATIVE HEALTHCARE TO A PATIENT POPULATION, all of the teachings of both of which are incorporated herein by reference.

STATEMENT RE: FEDERALLY SPONSORED RESEARCH/DEVELOPMENT

Not Applicable

BACKGROUND

The present invention is directed to methods for administering preventative healthcare to a patient population eligible to receive healthcare benefits in order to improve the quality component of treatment outcomes.

The healthcare industry is largely driven by compensation based on utilization. Hospitals, specialists and ancillary providers in the past were typically compensated based on utilization, which as a consequence led to increased utilization and wastage of healthcare resources. To prevent over-utilization and over-billing, payers (i.e., insurance companies and the like) began to capitate some of the services provided under managed care in order to limit the amount of dollars being spent. While this approach was generally effective in limiting total spending, such approach did not improve the quality component of treatment outcomes.

The Affordable Care Act, implemented as part of sweeping healthcare reform, introduced much needed changes in the healthcare industry. One major item was the introduction of Accountable Care Organizations (ACO's) that would attempt to address the problems being faced by the healthcare industry today which, among other things, included emphasizing the component of healthcare quality whereby reimbursement would be based not on utilization patterns but on treatment outcomes. For example, providers would receive additional compensation for performing post-discharge planning, working with other providers for preventing unnecessary emergency room admissions, made meaningful use of electronic healthcare records (EHR), implementing preventative healthcare measures, and the like.

Since the ACO concept is completely new for managed care organizations (e.g., HMO's) and/or traditional ways for providing care, a substantial need in the art has been created for new types of methods that, in the delivery of healthcare, enables healthcare providers and care coordinators such as nurses and case managers to render services in terms of "accountable care." Such practices would include additional documentation, coordination of care, increased focus on complex case management and disease management, automated updates of eligible beneficiaries and disease rosters, call logs, and the like. Such practices would further preferably integrate and interface with multiple data sources such as claims, beneficiaries' eligibility, pharmacy, lab data, accounting data and the like so as to create an aggregation of data compiled into a single database that would enable healthcare to be administered to achieve optimal patient outcomes and objective healthcare quality. In this regard, there is a substantial need in the art for methods that can enable healthcare to be administered with emphasis on quality, particularly with respect to preventative care whereby healthcare can be administered that can ensure that quality measures and preventative care, such as outstanding vaccinations and the like, can be administered to a specified patient population that is substantially more cost effective and efficient than current methods.

BRIEF SUMMARY

The present invention is directed to a population management application that provides a medium to focus on providing optimal preventive care to a specific patient population. Given the fact that healthcare providers spend only 15-20 minutes per office visit, they primarily focus on patients' chief complaints, resulting in very little focus on preventive care. This invention is designed to save providers' valuable time by integrating comprehensive set of healthcare data and providing outstanding "To Do" lists for each patient that results in an optimal delivery of healthcare.

Specifically, the present invention has the capability to measure the performance of Accountable Care Organizations (ACO) to provide preventative care and maintenance care of patients at risk for certain diseases against the quality measures set by Centers for Medicare/Medical Service (CMS). It calculates and summarizes an organization's scores for each quality measure against benchmarks and provides the workflow to improve quality of care.

To that end, the invention uses patients' enrollment information and compiles administrative and supplemental data from sources such as claims, pharmacy, clinical laboratory, and uploaded health records to generate the eligible population for each of the quality measures. Once the eligible population of members/enrollees (denominator) has been established, it calculates the set of patients that have fulfilled requirements for the measures (numerator) as well as the ones that have not met the criteria, also known as the non-compliant patients (numerator non-compliant or patients with "quality gaps").

According to a preferred embodiment, a central database is provided that is linked to a plurality of databases containing specific healthcare information concerning specific patients of a specified patient population. Such databases are directed to: electronic health records; pharmacy data, including prescriptions, number of prescriptions, duration of therapy, and the like; a lab database concerning all lab tests performed and their relevant findings for each patient in the patient population; and a further database related to claims and eligibility for each specific patient as provided and administered by any and all centers for Medicare/Medicaid services. The central database updates such information on a cyclical basis so as to provide the most current information available as may be accessed by healthcare providers and healthcare administrators.

From that collection of data, the patient population is first screened so as to identify an eligible patient population. Thereafter, those patients within the eligible population are compared to data compiled on the central database to ensure that each patient has complied with one or more healthcare requirements, and in particular any preventative healthcare measures that would be desirable to maintain optimal health and quality of healthcare delivery. In this regard, the present invention incorporates the use of standardized criteria related to numerous healthcare metrics related to specific preventative healthcare objectives, such as immunizations, disease screening and supervision of patients in at-risk populations prone to diabetes, hypertension, ischemic vascular disease, heart failure and coronary artery disease, such that objective healthcare criteria are met.

Once the specific needs of each patient within the eligible patient population are identified, measures are taken to ensure that each patient has been adequately treated and services rendered so that each specific member is deemed compliant or otherwise identified for further follow-up where more aggressive measures necessary to ensure compliance can be implemented.

BRIEF DESCRIPTION OF THE DRAWINGS

These as well as other features of the present invention will become more apparent upon reference to the drawings.

FIG. 3 is an exemplary screenshot identifying specific categories of preventative healthcare measures, the number of eligible patients within the patient population for which such preventative healthcare measures are available, and from that population those groups that have either complied or not complied with the requirements of such specific health measure and a percentage benchmark for the given population.

DETAILED DESCRIPTION

The detailed description set forth below is intended as a description of the presently preferred embodiment of the invention, and is not intended to represent the only form in which the present invention may be implemented or performed. The description sets forth the functions and sequences of steps for practicing the invention. It is to be understood, however, that the same or equivalent functions and sequences may be accomplished by different embodiments and that they are also intended to be encompassed within the scope of the invention. In this regard, the present invention is directed to methods for administering preventative healthcare to a patient population that ensures that the healthcare provided achieves optimal quality standards, particularly with respect to the administration of preventative healthcare to those patients in need of such services.

Figure 1:
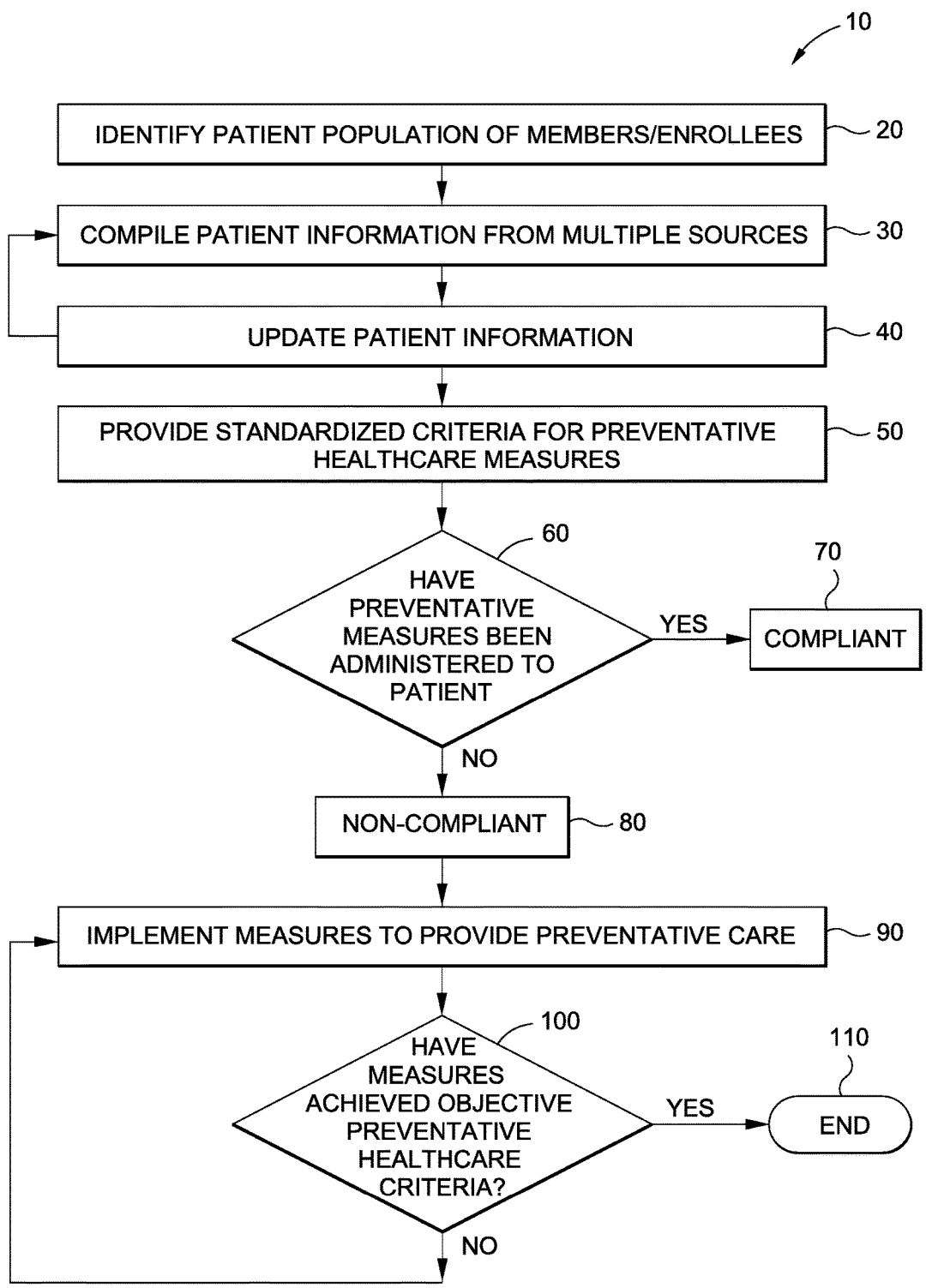
FIG. 1 is a flow chart depicting the general steps for performing the methods of the present invention for administering preventative healthcare to a patient population.

Referring now to the figures, and initially to FIG. 1, there is depicted a flow chart for administering preventative healthcare to a patient population that is exceptionally more efficient, more effective and greatly minimizes waste and conserves healthcare resources than prior art healthcare administration practices. As illustrated, the method 10 initially comprises the step 20 of identifying a patient population of members/enrollees of a given healthcare plan that are eligible to receive preventative care benefits. Such process of aggregating a patient population may be accomplished by any of a variety of known methods in the art and typically will involve enrolling members or enrollees within a given healthcare plan as is conventional practice.

Once identified, in step 30 a comprehensive collection of medical data is aggregated from multiple sources so that a comprehensive healthcare profile of each patient is captured and made available for use in assessing a patient's health and identifying which quality measures have or have not been met. Such multiple sources of data, discussed more fully in connection with FIG. 2 below, can consist of electronic healthcare records, pharmacy data, lab results and claims and eligibility information derived from Centers for Medicare/Medicaid Service (CMS). In order to ensure that such comprehensive medical data is kept as current as practical, step 40 is provided whereby each source of data from which the comprehensive data is compiled is updated on a periodic basis.

In step 50, there is provided a standardized criteria for preventative healthcare measures which are utilized as the standard by which preventative healthcare will be administered to eligible patients within the patient population. Such preventative healthcare measures may take any of a variety of standards that have been established in the art. Examples of such preventative healthcare standards may include the Centers for Medicare and Medicaid Services (CMMS), such as the five-star quality rating system; National Committee for Quality Assurance (NCQA) standards including the Healthcare Effectiveness Data and Information Set (HEDIS) quality measures; or Integrated Health Associations (IHA) Healthcare Pay for Performance (P4) program.

As will be appreciated by those skilled in the art, such preventative healthcare standards are set nationally, and further will generally define a population by age and, where appropriate, by gender or clinical condition. For purposes of practicing the present invention, step 50 further expressly takes into account twenty specific quality measures that are administered, including eight categories of preventative care, six categories related to the care and management of diabetes and six quality measures related to cardiac-specific health measures. In all such instances, each measure is provided with specific criteria for compliance and non-compliance according to a standardized level of care.

In step 60, a comparison is made to determine whether the eligible patients within a patient population have been provided the healthcare necessary to address the quality measures set forth in step 50, in which case if provided, such quality measures have been met and the process ends 70.

To the extent a specific quality measure has not been met for a given patient 80, measures are implemented to provide preventative care in step 70. Such measures include patient follow-up, patient education and the novel use of a "Boarding Pass" discussed more fully below that informs the patient of what measures need to be taken and how to go about addressing the same.

After having implemented such measures 90, follow-up procedures are established to determine whether or not the health quality measures have been met 100, in which case the methods end 110, or, if not, the implementation measures are pursued again until such time as the measure has been achieved or otherwise no longer applicable.

Figure 2:
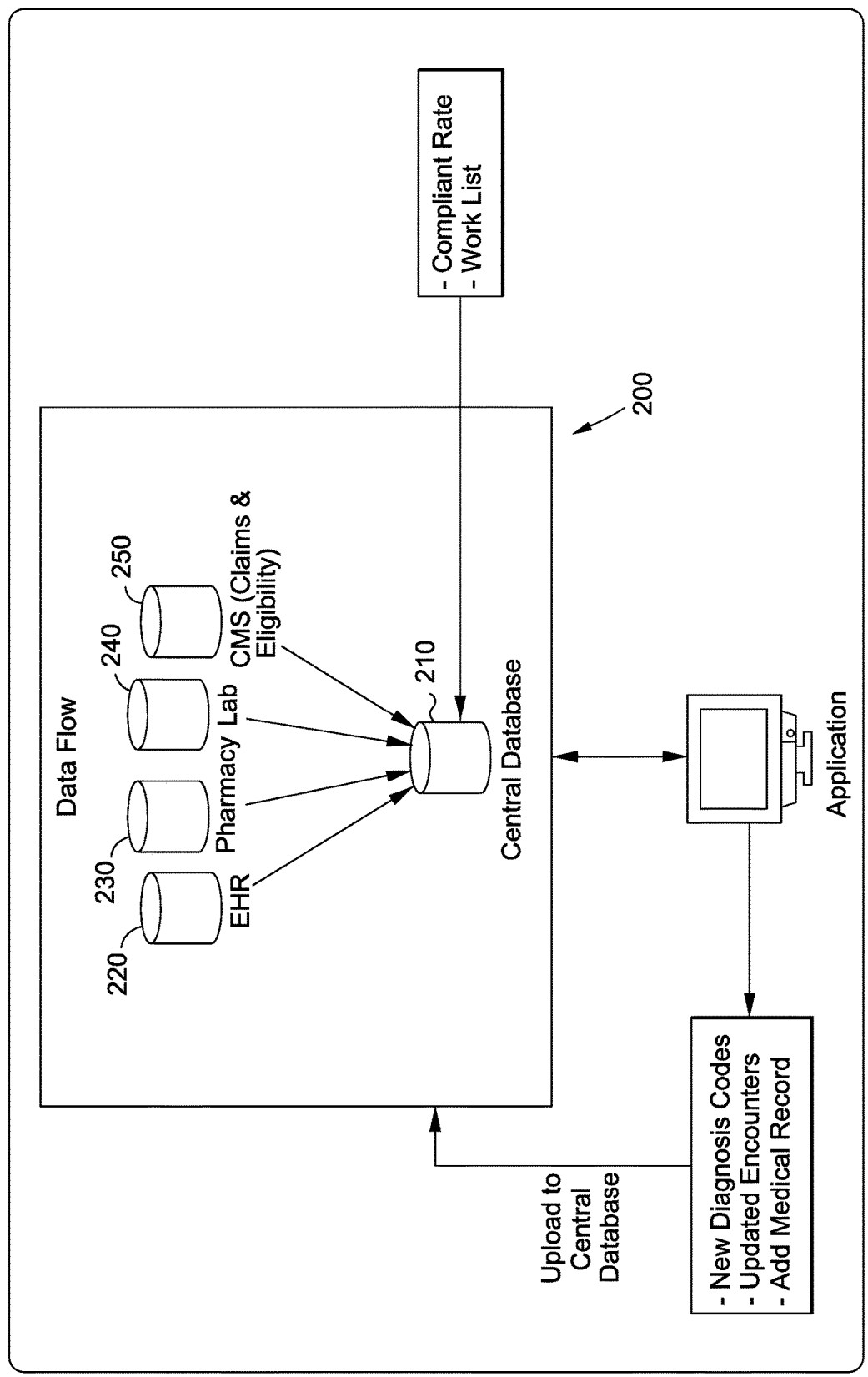
FIG. 2 is a schematic diagram depicting the computer/server architecture for implementing the methods of the present invention.

To help accomplish these steps, in FIG. 2 there is shown an exemplary architecture 200 for implementing the methods of the present invention according to a preferred embodiment. In this regard, there is provided a central database 210 that is linked to a plurality of databases associated with specific healthcare information for a given patient population. As illustrated, the central database 210 is connected to a database of electronic health records 220, pharmacy data 230, lab data 240, and data associated with centers for Medicare/Medicaid services 250, with respect to claims and eligibility information. Such information from the plurality of databases 220-250, which is well-known to those skilled in the art and capable of being readily and securely accessed, is operative to produce an aggregation of data within the central database 210 so that the applicable records and medical information for each member within the specified patient population is compiled and made readily accessible. Along those lines, the key to the practice of the present invention is updating the data within each respective database on a periodic basis. Table 1 below identifies these specific types of data that is aggregated in the central database, as well as the detailed data from which the information is derived and the frequency by which such information is updated.

TABLE 1

| # | Data Type | Source | Information Extracted | Frequency |
|---|---|---|---|---|
| 1 | Claims | CMS: Part A & B | Claim at the member level | Monthly |
| 2 | Membership | CMS | Member details and eligibility data | Monthly |
| 3 | Providers | CMS Claims Data | Provider details including geography | Monthly |
| 4 | Lab Results | Lab Vendors | Clinical Lab Results | Bi-Weekly |
| 5 | Pharmacy Data | CMS: Part D | Medication refills with dosage and other details | Monthly |

In addition to the foregoing categories of data and the sources from which they are derived, it is further contemplated that the central database 210 will further be provided with input means to include supplemental data concerning any other type of relevant medical information concerning a patient, whether it be clinical data, office visits and encounters and the like, which can be input into the system and will be integrated within the central database in real time. Such means of documenting and inputting such information are well-known and readily understood by those skilled in the art, and may be accomplished through inputting data through electronic medical records and the like.

As will further be readily understood and appreciated by those skilled in the art, the method by which the aforementioned databases are operatively connected to one another in order to send and retrieve the various types of information, as well as how such information is aggregated on the central database may be accomplished by a variety of computer hardware well-known to those skilled in the art. Exemplary of such hardware includes Microsoft SQO server 2005 and server 2008.

Given the foregoing architecture and interconnection between central database and plurality of databases coupled therewith, the discussion below and describes how an organization can use the present invention to measure and improve its rate of compliance with objective quality measures to optimally deliver healthcare. In this regard, the methods of the present invention are operative to accommodate the yearly ACO quality measures' changes made by CMS or any other objective quality criteria with minimal impact to the application design. Simply updating the tables with the changes would automatically reflect the changes for the quality measures by which healthcare delivery and subsequent quality are assessed.

To implement the present novel methodology, there is initially provided an eligible population to which healthcare benefits are made available (step 20 of FIG. 1), and from that population are identified compliant and non-compliant patients for each specific measure of healthcare, as well as the current score and benchmark. Such report provides an overview of an organization's performance on a set of 20 quality measures—8 Preventive Care, 6 Diabetes and 6 Cardiology related. A portion of an exemplary report specifying such data is shown in FIG. 3.

Each measure is provided with the specific criteria for compliance, non-compliance and exclusion of a patient. Table 2 identifies each specific preventative care measure of the 20 quality measures utilized in the practice of the present invention to determine whether or not sufficient preventative care is being administered to a sufficient percentage of the patient population.

TABLE 2

| # | PREVENTATIVE HEALTH MEASURES |
|---|---|
| 1 | Influenza immunization |
| 2 | Pneumococcal vaccination |
| 3 | Tobacco use and cessation |
| 4 | Tobacco use and cessation following cessation treatment |
| 5 | Depression screening |
| 6 | Colorectal cancer screening |
| 7 | Mammography screening |
| 8 | Blood pressure measurement |

All such preventative health measures are well-known in the art and routinely practiced using conventional medical procedures. Importantly, however, the methods of the present invention ensure that each patient's continuously updated medical records reflect if and when such preventative healthcare measures have been taken. If not, the methods herein can target a population for further follow-up and administration of such preventative healthcare measures. In this regard, the present invention is ideally suited for not only tracking the degree preventative healthcare measures are administered to a patient population, they can be utilized to determine if certain benchmarks have been set (for example, vaccination of a certain percentage of the patient population), and to proactively identify individual patients that may be prone to greater disease progression and potentially higher rates of morbidity and mortality that could otherwise be avoided through preventative care. Along those lines, the methods of the present invention may be practiced in conjunction with the teachings of Applicant's co-pending U.S. patent application Ser. No. 13/712,776, filed Dec. 12, 2012, entitled METHODS FOR OPTIMIZING MANAGED HEALTHCARE ADMINISTRATION AND ACHIEVING OBJECTIVE QUALITY STANDARDS, the teachings of which are expressly incorporated herein by reference.

In addition to the aforementioned preventative health measures, the present invention further contemplates administering preventative healthcare measures to at-risk patient populations afflicted with a particular condition. Specifically, the present invention contemplates administering "maintenance" care to eligible patients within the patient population afflicted with or at risk for developing diabetes, hypertension, ischemic vascular disease, heart failure and/or coronary artery disease. In this regard, there are six specific metrics related to patients at risk for diabetes that set forth criteria objectively considered appropriate for diabetes management. Table 3 sets forth the specific metrics to be met with respect to diabetes by the members in the eligible healthcare population deemed at risk, as determined by screening and via evaluation of patient data stored on the central database 210.

TABLE 3

| # | METRICS FOR AT-RISK POPULATION - DIABETES | OBJECTIVE |
|---|---|---|
| 1 | HbA1c (glycosylated hemoglobin) | 8% or less |
| 2 | Low density lipoprotein (LDL) | 100 mg/deciliter or less |
| 3 | Blood pressure (B) | Less than 140/90 |
| 4 | Confirmation of tobacco non-use | Cessation |
| 5 | Confirmation of daily aspirin use (optional) | Compliance |
| 6 | HbA1c (glycosylated hemoglobin) | 9% or less |

The methods of the present invention further contemplate implementing monitoring and management of patients within the eligible patient population at risk for certain cardiovascular conditions, namely, hypertension, ischemic vascular disease, heart failure and coronary artery disease. Table 4 below lists the specific metrics associated with each of the coronary conditions and the parameters to be met in managing such at-risk patients.

TABLE 4

| # | METRICS FOR AT-RISK POPULATION - CARDIAC | OBJECTIVE |
|---|---|---|
| 1 | Hypertension | Blood pressure control |
| 2 | Ischemic vascular disease | Full lipid profile and management of lowdensity lipoprotein (LDL) (100 mg/deciliter or less) |
| 3 | Ischemic vascular disease | Use of aspirin or another antithrombotic |
| 4 | Heart failure | Beta-blocker therapy for left ventricular systolic dysfunction (LVSD) |
| 5 | Coronary artery disease | Drug therapy for lowering low density lipoprotein (LDL) |
| 6 | Coronary artery disease | ACE inhibitor or ARB therapy (angiotensinconverting enzyme inhibitor with angiotensin-receptor blocker) |

In this regard, each specific quality measure has an objective criteria to be met, and once a given patient has been afforded that preventative care, that patient is identified as being compliant. In all the aforementioned categories, the patient population will typically involve all members 18 years or older, and preferably patients between the ages 18-75. Some specific categories, however, will apply to different segments of the patient population as will be appreciated by those skilled in the art. Specifically, pneumococcal vaccination will be directed to patients typically 65 or older; colorectal cancer screening will be directed to patients generally between the ages of 50 to 80; mammography screening will be directed to female patients generally between the ages of 42 and 69; and in the case of patients at risk for heart failure on beta-blocker therapy for left ventricular systolic dysfunction (LVSD), patients 18 years or older with LDEF less than 40% or with moderately or severe depressed left ventricular systolic function.

As discussed more fully below, by identifying the specific preventative healthcare quality measures to be afforded the eligible population, and by further making a determination how much of that population has been given such care, percentages can be derived as to how much of the population has been sufficiently treated. In turn, that percentage can be compared against a benchmark to ensure that adequate healthcare measures have been taken with respect to the aforementioned quality measures set forth in Tables 2-4.

Moreover, by expressly identifying twenty individual quality measures as set forth in Tables 2-4, coupled with the objective quality standards that must be met in order to determine compliance, the methods of the present invention readily provide a mechanism for continuously identifying which specific patients within the patient population health conditions warrant particular treatment for particular conditions, as is provided by the continuously updated medical information that is aggregated per step 30 of FIG. 1, but also identifies what specific action needs to be taken to ensure objectively appropriate healthcare has been administered to such patients. Such data makes it easy to thus identify a healthcare organization's performance level by measure and gives an idea as to which measures need to be focused on.

By virtue of being able to readily identify the eligible population or non-compliant population, gives healthcare providers the respective list with the demographic information of all the patients and their aligned providers. In this regard, patient data is derived to show the following areas: 1) Non-Compliant Measures; 2) Compliant Measures; and 3) Exclusions. In order to assess the degree by which preventative care is administered to the eligible patient population, the present invention contemplates measuring the percentage of patients that have received a specific standard of care and/or have attained a specific metric, as objectively set forth in a given standardized criteria, as compared to the entire patient population eligible to receive such preventative care. In this regard, the percentage is derived whereby the patient population is the denominator and the number of patients within that population that have attained the desired standard of care being the numerator. A benchmark is then established whereby a specific percentage of the population has been provided with a given preventative care measure versus the entire eligible patient population. A standard of 95% would typically represent that an optimal portion of the patient population has received adequate preventative care. Other benchmark percentages may further be utilized to measure preventative healthcare administration. For example, 90% may represent a base line level for a given healthcare standard of preventative healthcare and 85% may be indicative of suboptimal delivery of a given preventative healthcare measure.

Such information gives healthcare providers an overall picture of a specific patient's level of compliance and a list of measures that need to be focused on, as well as the claims, pharmacy and lab data that made that patient qualify for treatment.

Such information further enables users to identify and communicate with those patients regarding their non-compliance and implements measures that ensure that the patients are aware of their preventive health needs and requirements. In this regard, the methods of the present invention not only enable a specific segment of the patient population to be readily identified that is deficient in receiving preventative care, such methods further enable specific individuals within the patient population to be selectively tracked and targeted for an individualized patient approach whereby proactive measures can be taken to ensure that a specific patient is afforded sufficient preventative care so as to potentially ward off potential disease progression and the like. For example, healthcare providers can print out "Boarding Pass" which is a pre-designed letter template listing all the non-compliant measures for that patient. Such letter can be mailed out to the patients or handed to them in person to make them more proactively involved in their health care.

Such contact with the patient also enables the methods disclosed herein to capture pertinent medical information that is missing from claims, pharmacy, and lab information for the patient to change their status from non-compliant to compliant/excluded for a given measure. The application also allows the user to upload supporting documentation which can be retrieved at any time via the central database, all of which can go to determining whether the patient becomes compliant with regard to a given measure.

The methods disclosed herein, using known search techniques, can further be filtered by region, service area and network, or can be viewed at a company level. The advantage of this filtering system is that users can see and compare the rate of compliance between different campuses/networks as may be desired. It also makes it easier to identify outliers and quickly address problems that may exist only in certain geographies or regions. The present invention offers the capability to group several networks into service areas and analyze performance at the service area level.

In all cases, however, the ultimate objective is to ensure that the objective criteria for each quality measure are met with respect to each eligible patient within the patient population. Attempts to provide such care are implemented in the aforementioned manner until such time as each patient can be deemed compliant for a particular quality measure and/or an acceptable percentage of the eligible patient population has been treated. As is also contemplated, to the extent a particular member is no longer within the patient population and/or is no longer eligible to receive such preventative care measures, it will be understood and readily appreciated that the methods contemplate any such individual will be excluded from the methods whereby the specific patient is entirely removed from the patient population or, alternatively, the application of the objective quality measures are not compared to a specific patient or a specific condition of a patient, in which case no determination is made whether or not a patient is compliant or non-compliant for a given condition. As will be appreciated by those skilled in the art, such mechanism thus enables the methods to be practiced solely in connection with eligible patients within the patient population so as to conserve healthcare resources, prevent waste and ensure that only those patients eligible to receive care adhering to the objective quality standards actually do get the care to which they are entitled.

The detailed description set forth below is intended as a description of the presently preferred embodiment of the invention, and is not intended to represent the only form in which the present invention may be implemented or performed. The description sets forth the functions and sequences of steps for practicing the invention. It is to be understood, however, that the same or equivalent functions and sequences may be accomplished by different embodiments and that they are also intended to be encompassed within the scope of the invention.

What is claimed is:

1. A method of administering preventative healthcare to a patient population, the method comprising:
storing an aggregation of electronic health records, pharmacy data, lab data, and health insurance data in a central database for each of a plurality of patients;
updating the central database to reflect changes in the electronic health records, pharmacy data, lab data, and health insurance data at predetermined intervals;
storing a plurality of standardized preventative healthcare measures in one or more tables, each of the standardized preventative healthcare measures stored in association with corresponding criteria for compliance, non-compliance, and exclusion of a patient;
periodically updating the one or more tables to reflect changes in the standardized preventative healthcare measures;
for each of the plurality of patients, comparing the aggregation of electronic health records, pharmacy data, lab data, and health insurance data stored in the central database to the exclusion criteria of each of the plurality of standardized preventative healthcare measures to generate, for each of the plurality of standardized preventative healthcare measures, a set of eligible patients associated with the standardized preventative healthcare measure;
for each of the eligible patients associated with a standardized preventative healthcare measure from among the plurality of standardized preventative healthcare measures, comparing the aggregation of electronic health records, pharmacy data, lab data, and health insurance data stored in the central database to the compliance and non-compliance criteria of the standardized preventative healthcare measure;
displaying a summary report on a graphical user interface, the summary report including, for each of the plurality of standardized preventative healthcare measures, an indication of the number of patients, from among the plurality of patients, whose aggregation of electronic health records, pharmacy data, lab data, and health insurance data meets the non-compliance criteria of the standardized preventative healthcare measure as determined by said comparing steps, the summary report further including, for each of the plurality of standardized preventative healthcare measures, an indication of the number of patients, from among the plurality of patients, whose aggregation of electronic health records, pharmacy data, lab data, and health insurance data meets the compliance criteria of the standardized preventative healthcare measure as determined by said comparing steps;
generating, in response to user interaction with a link associated with one of the indications, a list of non-compliant patients for the corresponding standardized preventative healthcare measure, the list of non-compliant patients including each patient, from among the plurality of patients, whose aggregation of electronic health records, pharmacy data, lab data, and health insurance data meets the non-compliance criteria of the standardized preventative healthcare measure as determined by said comparing steps; and
administering a vaccination to a patient on the list of non-compliant patients.

2. The method of claim 1, wherein the summary report further includes, for each of the plurality of standardized preventative healthcare measures, an indication of a rate of compliance based on i) the number of patients whose aggregation of electronic healthcare records, pharmacy data, lab data, and health insurance data meets the compliance criteria and ii) the number of patients in the set of eligible patients.

3. The method of claim 2, wherein the indication of the rate of compliance comprises a percentage of the set of eligible patients whose aggregation of electronic healthcare records, pharmacy data, lab data, and health insurance data meets the compliance criteria.

4. The method of claim 2, wherein the summary report further includes an indication of a benchmark for comparison with the rate of compliance.

5. The method of claim 1, wherein the summary report further includes, for each of the plurality of standardized preventative healthcare measures, an indication of the number of patients in the set of eligible patients.

\* \* \* \* \*